United States Patent
Zhang et al.

(10) Patent No.: US 10,301,242 B2
(45) Date of Patent: May 28, 2019

(54) METHOD FOR EXTRACTING CANNABIDIOL FROM CANNABIS

(71) Applicant: Yunnan Hansu bio-technology Co.,Ltd, Kunming (CN)

(72) Inventors: Ke Zhang, Kunming (CN); Xin Tan, Kunming (CN); Weibo Gao, Kunming (CN); Tanran Chang, Kunming (CN)

(73) Assignee: Yunnan Hansu bio-technology Co.,Ltd, Kunming (CN)

( * ) Notice: Subject to any disclaimer, the term of this patent is extended or adjusted under 35 U.S.C. 154(b) by 0 days.

(21) Appl. No.: 15/781,795

(22) PCT Filed: Jan. 21, 2017

(86) PCT No.: PCT/CN2017/071993
§ 371 (c)(1),
(2) Date: Jun. 6, 2018

(87) PCT Pub. No.: WO2018/032727
PCT Pub. Date: Feb. 22, 2018

(65) Prior Publication Data
US 2018/0362429 A1    Dec. 20, 2018

(30) Foreign Application Priority Data
Aug. 16, 2016   (CN) .......................... 2016 1 0674119

(51) Int. Cl.
| | | |
|---|---|---|
| *C07C 37/68* | (2006.01) | |
| *C07C 37/82* | (2006.01) | |
| *C07C 37/84* | (2006.01) | |
| *C07C 39/23* | (2006.01) | |

(52) U.S. Cl.
CPC ............ *C07C 37/685* (2013.01); *C07C 37/68* (2013.01); *C07C 37/82* (2013.01); *C07C 37/84* (2013.01); *C07C 39/23* (2013.01); *C07C 2601/16* (2017.05)

(58) Field of Classification Search
CPC ....... C07C 37/685; C07C 37/82; C07C 37/84; C07C 2601/16
See application file for complete search history.

(56) References Cited

U.S. PATENT DOCUMENTS

| | | |
|---|---|---|
| 6,403,126 B1 | 6/2002 | Webster et al. |
| 2006/0167283 A1 | 7/2006 | Flockhart et al. |

FOREIGN PATENT DOCUMENTS

| | | | | |
|---|---|---|---|---|
| CN | 103739585 | * | 4/2014 | ........... C07D 311/80 |
| CN | 103739585 A | | 4/2014 | |
| CN | 104277917 | * | 1/2015 | ............... C11B 9/02 |
| CN | 104277917 A | | 1/2015 | |
| CN | 105505565 A | | 4/2016 | |
| CN | 105535111 A | | 5/2016 | |
| CN | 106278828 A | | 1/2017 | |

OTHER PUBLICATIONS

International Search Report and Written Opinion of the International Search Authority dated Mar. 8, 2017 of corresponding International application No. PCT/CN2017/071993; 9 pgs.

* cited by examiner

*Primary Examiner* — Rosalynd A Keys
(74) *Attorney, Agent, or Firm* — Maier & Maier, PLLC

(57) ABSTRACT

A method of extracting cannabidiol from hemp. The method may include the following steps: performing grinding and drying on an extraction part of the hemp to obtain crude drug powder; extracting the crude drug powder with 30-100% (V/V) ethanol to obtain an extracting solution; concentrating the extracting solution to obtain an extractum; performing water precipitation on the extractum to remove impurities, thereby obtaining a water precipitation solution; centrifuging the water precipitation solution, and adding 10-100% (V/V) ethanol to dissolve the obtained precipitate, thereby obtaining a precipitate alcohol solution; performing column chromatography on the precipitate alcohol solution; concentrating the eluate obtained by elution after column chromatography, and adding ethanol for supersaturation and dissolution to obtain a crystal; adding purified water or ethanol to wash the crystal, thereby obtaining a primary product; and uniformly mixing the primary product with purified water, and drying to obtain the cannabidiol.

16 Claims, 5 Drawing Sheets

METHOD FOR EXTRACTING CANNABIDIOL FROM CANNABIS

CROSS-REFERENCE TO RELATED APPLICATIONS

The present patent application claims benefit and priority to Chinese Patent Application No. 201610674119.6 filed on Aug. 16, 2016, in the Chinese Patent Office, the disclosure of which is incorporated herein by reference. Further, this application is the National Phase application of International Application No. PCT/CN2017/071993 filed Jan. 21, 2017, which designates the United States and was published in China.

TECHNICAL FIELD

The present invention relates to a method of extracting cannabidiol from hemp, particularly to a method of extracting cannabidiol from industrial hemp flowers and leaves.

BACKGROUND

Hemp (*Cannabis sativa* L.), also known as marijuana, is a plant in the *Cannabis* genus which belongs to the family Cannabaceae, and has important agricultural and medicinal value. The hemp contains a toxic ingredient THC (tetrahydrocannabinol) which can make people to be hallucinated and addicted. The hemp can be used as a drug and has been banned for a long period of time.

The economic and medicinal value of hemp is extremely high, raw hemp dedicated to industrial use is simply referred to as 'industrial hemp', and its tetrahydrocannabinol (THC) content in the hemp flowers and leaves in the growth period is less than three-thousandths, so the industrial hemp cannot extract toxic tetrahydrocannabinol or be used directly as drug. Therefore, it can be legally subjected to large-scale cultivation and industrial development and utilization.

At present, more than 500 substances have been separated from hemp plants, among which there are at least 86 cannabinoids. Cannabinoids are a unique class of substances in the hemp plants and main active ingredients in hemp plants. Research on cannabinoids has always been a hotspot in hemp research. The main cannabinoids in hemp plants are tetrahydrocannabinol (THC), cannabinol (CBN), cannabidiol (CBD), cannabigerol (CBG), cannabichromene (CBC), etc., among which the top three account for more than 90% of cannabinoids.

In recent years, research on active ingredients of hemp found that cannabidiol is not neurotoxic and has significant medicinal value. Related pharmacological research has shown that it can hinder the effect of tetrahydrocannabinol on the human nervous system, has pharmacological activities such as anti-spasm, anti-rheumatoid arthritis and anti-anxiety, and thus, has great industrial development value.

At present, there are some reports in the public information about methods of extracting cannabidiol or extracting cannabidiol-containing industrial hemp oil from industrial hemp. For example, CN104277917A discloses a method and a device for extracting cannabidiol-rich industrial hemp essential oil; and a screener, an oven, and a soaking pool, a rotary evaporator, an ultrasonic stirring tank, a disk centrifuge, a first climbing film evaporator, a proportioning tank, a pressure chromatographic silica gel column, an eluate tank, a second climbing film evaporator, a rotary evaporator, a finished product tank and a solvent recovery tank that are sequentially connected by pipelines are adopted to sequentially perform operation steps of screening, baking, leaching, retreatment, filtration, monitoring, loading, chromatography, concentration and finished production acquisition for the industrial hemp, thereby finally extracting industrial hemp essential oil which is rich in the effective ingredient cannabidiol. CN 105505565 A discloses a method of extracting cannabidiol-rich industrial hemp oil, which uses a supercritical carbon dioxide fluid to extract industrial hemp oil from industrial hemp; and in the extraction process, cooled industrial hemp powder is put into a material vat of an extraction kettle, and $CO_2$ gas is injected into the extraction kettle to keep such temperature and pressure in the extraction kettle that the $CO_2$ gas contacts the raw material in the supercritical state, so that industrial hemp oil and other ingredients in the industrial hemp powder are dissolved in the supercritical fluid, and thus, the fluid containing cannabidiol and other ingredients is subjected to throttling expansion to enter a separation kettle from the extraction kettle to be resolved, thereby obtaining and collecting the industrial hemp oil. CN 105535111 A discloses a preparation method of extracting a cannabidiol-rich hemp extractum from industrial hemp flowers and leaves, which includes the following steps: performing dry heat treatment on hemp flowers and leaves, and obtaining a cannabidiol-rich crude extractum by a subcritical butane extraction technique with ethanol as an entrainer; dissolving the crude extractum in an ethanol solution of a certain proportion, and performing low-temperature winterization; centrifuging or filtering to remove wax; adding activated carbon into the supernate to perform decolorization, and performing filtration treatment; and finally, performing rotary evaporation on the obtained filtrate to remove the ethanol, thereby obtaining the CBD-rich hemp extractum. The prior art CN 103739585 A, which is the closest to the present invention, discloses a technique for extracting cannabidiol (CBD) from industrial hemp; the technique includes the following steps: picking of flowers and leaves, drying, grinding, soaking extraction, and concentration and separation; and through comparative studies, the method of extracting cannabidiol from industrial hemp mentioned in the prior art mainly has the following problems:

1) due to the complexity of cannabinoids in the original plant and the existence of many polarity-like ingredients, the purity of cannabidiol in the final product is not high after extraction and refinement by the traditional method;

2) after extraction and purification, tetrahydrocannabinol, a psychotoxic ingredient, can still be detected, so the product safety cannot be guaranteed, product circulation is limited, and industrial production and applications are affected; and 3) since the solubility of cannabidiol in organic solvents is higher than that in ethanol, in order to increase the yield of cannabidiol, the industry usually uses a toxic organic solvent, such as petroleum ether, n-hexane, dichloromethane or the like, in the technical steps of extraction, leaching, purification and the like, however, the use of such organic solvents may do harm to the environment, and the solvent residues in the final product cannot be completely removed, which also affects the product safety.

Therefore, there is currently an urgent need to provide a method of preparing high-purity tetrahydrocannabinol-free cannabidiol without residues of poor organic solvents. The preparation method should also satisfy the industrial development demands of energy saving, environment friendliness and economy.

SUMMARY

The present invention aims to provide a method of extracting cannabidiol from hemp, so as to solve the problems of low purity, psychotoxic ingredient tetrahydrocannabinol residues and the like in the cannabidiol extracted by the prior art.

In order to achieve the goal, the present invention provides a method of extracting cannabidiol from hemp. The method includes the following steps:

1) performing grinding and drying on an extraction part of hemp to obtain crude drug powder;

2) extracting the crude drug powder with 30-100% (V/V) ethanol to obtain an extracting solution;

3) concentrating the extracting solution to obtain an extractum;

4) performing water precipitation on the extractum to remove impurities to obtain a water precipitation solution;

5) centrifuging the water precipitation solution, and adding 10-100% (V/V) ethanol to dissolve the precipitate obtained by centrifuging, thereby obtaining a precipitate alcohol solution;

6) performing column chromatography on the precipitate alcohol solution;

7) concentrating the eluate obtained in step 6), and adding ethanol for supersaturation and dissolution to obtain a crystal;

8) adding purified water or ethanol to wash the crystal, thereby obtaining a primary product; and 9) uniformly mixing the primary product obtained in step 8) with purified water, and drying to obtain the cannabidiol.

Preferably, the hemp in the present invention is selected from one or combination of more than two of industrial hemp, intermediate hemp or medicinal hemp.

Preferably, the extraction part in step 1) in the present invention is selected from one or combination of more than two of hemp flowers, hemp leaves, hemp roots, hemp stalk cores and hemp seed cakes. Preferably, the extraction part in step 1) in the present invention is hemp flowers and hemp leaves.

Preferably, the hemp extraction part in step 1) in the present invention is ground to 10-80 meshes, such as 10 meshes, 12 meshes, 14 meshes, 16 meshes, 18 meshes, 20 meshes, 25 meshes, 30 meshes, 35 meshes, 40 meshes, 45 meshes, 50 meshes, 60 meshes, 70 meshes, 80 meshes or the like, further preferably 20-60 meshes, more preferably 25-50 meshes, and most preferably 40 meshes. In a typical implementation of the present invention, by grinding the hemp flowers and leaves to the above-mentioned range of meshes in step 1), the cannabidiol can be sufficiently extracted in the subsequent ethanol extraction step.

Preferably, the temperature of drying after grinding the hemp extraction part in step 1) of the present invention is 60-200° C., such as 60° C., 60.1° C., 61° C., 64° C., 65° C., 68° C., 70° C., 72° C., 75° C., 77° C., 80° C., 83° C., 85° C., 86° C., 87.5° C., 90° C., 90.5° C., 92.5° C., 95° C., 99° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C. or the like, further preferably 80-180° C., and more preferably 100-150° C.

Preferably, the time of drying after grinding the hemp extraction part in step 1) of the present invention is 0.5-3 h, such as 0.5 h, 0.6 h, 0.7 h, 0.8 h, 0.9 h, 1 h, 1.1 h, 1.2 h, 1.3 h, 1.4 h, 1.5 h, 1.6 h, 1.7 h, 1.8 h, 1.9 h, 2 h, 2.1 h, 2.2 h, 2.3 h, 2.4 h, 2.5 h, 2.6 h, 2.7 h, 2.8 h, 2.9 h or 3 h, further preferably 1-2.5 h, and more preferably 1.5-2 h.

Further, the drying after grinding the hemp extraction part in step 1) of the present invention preferably continues to water content of 5% or below. In a typical implementation of the present invention, under the above-mentioned drying conditions in step 1), the drying efficiency of the hemp flowers and leaves is high, the drying effect is good, and the effective ingredients in the hemp flowers and leaves can not be destroyed.

In a typical implementation of the present invention, the step 1) includes: grinding hemp flowers and leaves to 10-80 meshes, and drying at the temperature of 60-200° C. for 0.5-3 h until the water content is 5% or below, thereby obtaining the crude drug powder.

Preferably, the amount of the ethanol in step 2) of the present invention is 2-8 times the amount of the crude drug powder, such as 2 times, 2.2 times, 2.5 times, 2.7 times, 3 times, 3.5 times, 4 times, 4.5 times, 5 times, 5.5 times, 6 times, 6.5 times, 7 times, 7.5 times or 8 times the amount of the crude drug powder, further preferably 3-7 times the amount of the crude drug powder, and more preferably 4-6 times the amount of the crude drug powder.

Preferably, the number of times of the ethanol extraction in step 2) of the present invention is 1-3.

Preferably, the extraction manner of the ethanol extraction in step 2) of the present invention is reflux extraction, ultrasonic extraction and/or soaking extraction.

Further preferably, the time length of the reflux extraction is 0.5-3 h each time; the time length of the ultrasonic extraction is 0.1-1 h each time; and the time length of the soaking extraction is 0.5-5 h each time.

In a typical implementation of the present invention, step 2) includes: extracting the crude drug powder with 30-100% (V/V) ethanol which is 2-8 times the amount of the crude drug powder for 1-3 times, to obtain an extracting solution.

Preferably, in step 3) of the present invention, the extracting solution is concentrated until the relative density is measured to be 1.05-1.35 at 50° C.

Preferably, the amount of water for the water precipitation in step 4) of the present invention is 1-10 times the amount of the crude drug powder, such as 1 times, 1.1 times, 1.2 times, 1.3 times, 1.4 times, 1.5 times, 1.6 times, 1.7 times, 1.8 times, 1.9 times, 2 times, 2.25 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times or 10 times the amount of the crude drug powder, further preferably 2-8 times the amount of the crude drug powder, and more preferably 3-6 times the amount of the crude drug powder.

Preferably, the temperature of the water precipitation in step 4) of the present invention is 0-20° C., such as 0° C., 0.1° C., 0.5° C., 0.8° C., 1° C., 1.2° C., 1.5° C., 1.75° C., 2° C., 2.5° C., 3° C., 3.5° C., 4° C., 4.5° C., 5° C., 5.5° C., 6° C., 6.5° C., 7° C., 7.5° C., 8° C., 8.5° C., 9° C., 9.5° C., 10° C., 10.5° C., 11° C., 11.5° C., 12° C., 12.5° C., 13° C., 13.5° C., 14° C., 14.5° C., 15° C., 15.5° C., 16° C., 16.5° C., 17° C., 17.5° C., 18° C., 18.5° C., 19° C., 19.5° C. or 20° C., further preferably 2-18° C., and more preferably 5-15° C.

Preferably, the time length of the water precipitation in step 4) of the present invention is 1-48 h, such as 1 h, 1.1 h, 1.3 h, 1.5 h, 1.9 h, 2 h, 2.5 h, 3 h, 3.5 h, 4 h, 4.5 h, 5 h, 5.5 h, 6 h, 6.5 h, 7 h, 7.5 h, 8 h, 8.5 h, 9 h, 9.5 h, 10 h, 10.5 h, 11 h, 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h, 31 h, 32 h, 33 h, 34 h, 35 h, 36 h, 37 h, 38 h, 39 h, 40 h, 41 h, 42 h, 43 h, 44 h, 45 h, 46 h, 47 h or 48 h, further preferably 2-36 h, and more preferably 5-30 h.

In a typical implementation of the present invention, step 4) includes: performing water precipitation at the temperature of 0-20° C. for 1-48 h by using purified water which is 1-10 times the amount of the crude drug powder, thereby obtaining a water precipitation solution.

Preferably, the filler of the chromatographic column used in the column chromatography in step 6) of the present invention includes, but not limited to one or more of macroporous resin, MCI resin and octadecyl silane bonded silica gel, further preferably macroporous resin and/or MCI resin, and more preferably MCI resin. The MCI resin is a novel resin designed by Mitsubishi Chemical based on Diaion and Sepabeads macroporous resins, and the particle size is only 75-150 micrometers. The macroporous resin includes, but not limited to one or more of AB-8, D-101, XDA-8, LSA-7, D-941, DM-130, ADS-17, SP-825 and HPD-600.

Preferably, the column chromatography in step 6) of the present invention includes: performing gradient elution on a chromatographic column by using an elution solvent; the elution solvent is preferably ethanol and/or water; and further preferably, the step of gradient elution includes: performing elution by using 0-30% (V/V) ethanol for impurity removal, and then performing elution by using 40-80% (V/V) ethanol to obtain a target product part. More preferably, the step of gradient elution includes: performing elution by using 0-30% (V/V) ethanol for impurity removal, then performing elution by using 40-80% (V/V) ethanol to obtain the target product part, and finally, performing elution by using 90-95% (V/V) to regenerate the chromatographic column. By performing the above-mentioned step of gradient elution, the target product part has high purity, and the chromatographic column can be continuously regenerated and recycled.

Preferably, the concentrating the eluate obtained in step 6) in step 7) of the present invention is to concentrate the eluate until the relative density is measured to be 1.05-1.35 at 50° C.

Preferably, the temperature of adding the ethanol for supersaturation and dissolution in step 7) of the present invention is 10-80° C., such as 10° C., 10.1° C., 10.5° C., 10.7° C., 11° C., 12° C., 15° C., 18° C., 20° C., 23° C., 25° C., 26° C., 29° C., 30° C., 35° C., 37° C., 40° C., 40.5° C., 45° C., 50° C., 55° C., 60° C., 65° C., 70° C., 75° C. and 80° C., further preferably 20-60° C., and more preferably 30-50° C.

Preferably, the concentration of the ethanol in step 7) of the present invention is 60-100% (V/V).

Further preferably, step 7) of the present invention also includes a step of recovering ethanol in the eluate.

In a typical implementation of the present invention, step 7) includes: concentrating the eluate obtained in step 6) until the relative density is measured to be 1.05-1.35 at 50° C., and adding 60-100% (V/V) ethanol for supersaturation and dissolution at the temperature of 10-80° C. to obtain a crystal.

In a preferable implementation of the present invention, step 7) includes: concentrating the eluate obtained in step 6) until the relative density is measured to be 1.05-1.35 at 50° C., recovering the ethanol in the eluate, and adding 60-100% (V/V) ethanol for supersaturation and dissolution at the temperature of 10-80° C. to obtain a crystal.

Preferably, the temperature of the washing in step 8) of the present invention is 0-24° C., such as 0° C., 0.1° C., 0.5° C., 0.8° C., 1° C. 1.5° C., 2° C., 2.5° C., 3° C. 3.5° C., 4° C., 4.5° C., 5° C. 5.5° C., 6° C., 6.5° C., 7° C., 7.5° C., 8° C., 8.5° C., 9° C., 9.5° C., 10° C., 11° C., 12° C., 13° C., 14° C., 15° C., 16° C., 17° C., 18° C., 19° C., 20° C., 21° C., 22° C., 23° C. and 24° C., further preferably 5-20° C., and more preferably 10-15° C.

Preferably, the concentration of the ethanol in step 8) of the present invention is 5-40% (V/V).

In a typical implementation of the present invention, step 8) includes: adding purified water or 5-40% (V/V) ethanol at the temperature of 0-24° C. to wash the crystal, thereby obtaining a primary product.

Preferably, the drying manner in step 9) of the present invention includes, but not limited to, one or more of spray drying, vacuum drying, freeze drying, near-infrared drying and microwave drying.

Preferably, the temperature of the drying in step 9) of the present invention does not exceed 65° C.

Further preferably, step 9) in the present invention also includes a step of grinding the obtained cannabidiol into powder; the grinding manner includes jet grinding and/or cryogenic grinding; and the material temperature during grinding does not exceed 65° C.

In a preferable implementation of the present invention, the present invention provides a method of extracting cannabidiol from hemp, which includes the following steps:

1) grinding an extraction part of hemp to 10-80 meshes, and drying at the temperature of 60-200° C. for 0.5-3 h until the water content is 5% or below, thereby obtaining crude drug powder;

2) extracting the crude drug powder with 30-100% (V/V) ethanol which is 2-8 times the amount of the crude drug powder for 1-3 times, to obtain an extracting solution;

3) concentrating the extracting solution until the relative density is measured to be 1.05-1.35 at 50° C., thereby obtaining an extractum;

4) performing water precipitation at the temperature of 0-20° C. for 1-48 h by using purified water which is 1-10 times the amount of the crude drug powder, so as to remove impurities, thereby obtaining a water precipitation solution;

5) centrifuging the water precipitation solution, and adding 10-100% (V/V) ethanol to dissolve the precipitate obtained by centrifuging, thereby obtaining a precipitate alcohol solution;

6) performing column chromatography on the precipitate alcohol solution, wherein a filler used in a chromatographic column of the column chromatography includes one or more of macroporous resin, MCI resin and octadecyl silane bonded silica gel, and the column chromatography specifically includes the following steps: performing elution with 0-30% (V/V) ethanol for impurity removal, performing elution with 40-80% (V/V) ethanol to obtain a target product part, and finally, performing elution with 90-95% (V/V) ethanol to regenerate the chromatographic column;

7) concentrating the eluate obtained in step 6) until the relative density is measured to be 1.05-1.35 at 50° C., and adding 60-100% (V/V) ethanol for supersaturation and dissolution at the temperature of 10-80° C. to obtain a crystal;

8) adding purified water or 5-40% (V/V) ethanol at the temperature of 0-24° C. to wash the crystal, thereby obtaining a primary product; and 9) uniformly mixing the primary product in step 8) with purified water, and drying at the temperature of not more than 65° C. to obtain the cannabidiol.

In another preferable implementation of the present invention, the present invention provides a method of extracting cannabidiol from hemp flowers and leaves, which includes the following steps:

1) grinding hemp flowers and leaves to 10-80 meshes, and drying at the temperature of 60-200° C. for 0.5-3 h until the water content is 5% or below, thereby obtaining crude drug powder;

2) extracting the crude drug powder with 30-100% (V/V) ethanol which is 2-8 times the amount of the crude drug powder, 1-3 times, to obtain an extracting solution;

3) concentrating the extracting solution until the relative density is measured to be 1.05-1.35 at 50° C., thereby obtaining an extractum;

4) performing water precipitation for the extractum at the temperature of 0-20° C. for 1-48 h by using purified water which is 1-10 times the amount of the crude drug powder, so as to remove impurities, thereby obtaining a water precipitation solution;

5) centrifuging the water precipitation solution, and adding 10-100% (V/V) ethanol to dissolve the precipitate obtained by centrifuging, thereby obtaining a precipitate alcohol solution;

6) performing column chromatography on the precipitate alcohol solution, wherein a filler used in a chromatographic column of the column chromatography includes one or more of macroporous resin, MCI resin and octadecyl silane bonded silica gel, and the column chromatography specifically includes the following steps: performing elution with 0-30% (V/V) ethanol for impurity removal, performing elution with 40-80% (V/V) ethanol to obtain a target product part, and finally, performing elution with 90-95% (V/V) ethanol to regenerate the chromatographic column;

7) concentrating the eluate obtained in step 6) until the relative density is measured to be 1.05-1.35 at 50° C., recovering the ethanol in the eluate, and adding 60-100% (V/V) ethanol for supersaturation and dissolution at the temperature of 10-80° C. to obtain a crystal;

8) adding purified water or 5-40% (V/V) ethanol at the temperature of 0-24° C. to wash the crystal, thereby obtaining a primary product; and 9) uniformly mixing the primary product in step 8) with purified water, drying at the temperature of not more than 65° C., and performing grinding to obtain the cannabidiol.

It should be noted that the description "2-8 times the amount of the crude drug powder" or "1-10 times the amount of the crude drug powder" in the application means that the volume of the adopted solvent, such as ethanol or water, is 2-8 times or 1-10 times the mass of the crude drug powder, for example, the amount of the crude drug powder is 1 g, and the amount of the extraction solvent ethanol is 2 ml-8 ml.

According to the extraction of cannabidiol (CBD) from hemp in the present invention, the technical scheme that breaks the conventional understanding in the field is adopted; by abandoning solvents such as petroleum ether, n-hexane and methylene chloride that have high solubility in cannabidiol (CBD) in the prior art in the technique, using ethanol with a relatively low solubility as an extraction solvent in the whole process of the technique and combining with an improved extraction technique, it is unexpectedly detected that the yield and purity of the cannabidiol (CBD) are obviously increased, thereby overcoming the technical prejudice on the selection of the extraction solvent and the product yield in the art; and meanwhile, the psychotoxic ingredient tetrahydrocannabinol is not detected in finished product, so that the safety of the product is guaranteed. In addition, the used reagent is ethanol and water, thereby reducing the effects on the environment, operating personnel and product solvent residues. The filler of the chromatographic column can be recycled, so that the overall production cost is lowered, and the environmental pollution caused by the filler waste is reduced, thereby benefiting industrial production.

DESCRIPTION OF DRAWINGS

The accompanying drawings, which constitute a part of this application, are used to provide a further understanding of the present invention, and the exemplary embodiments of the present invention and the description thereof are used to explain the present invention and do not constitute improper limitations to the present invention. In the accompanying drawings.

DETAILED DESCRIPTION

Figure 1:
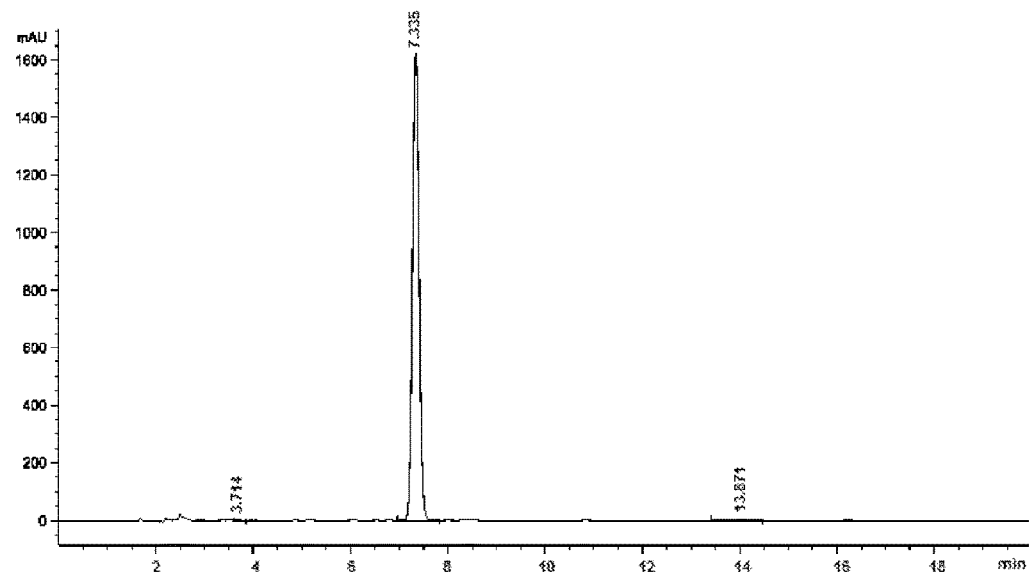
FIG. 1 shows a chromatogram of the product 1.

It should be noted that the embodiments in the application and the features in the embodiments can be combined with each other under the condition of no conflict. The present invention will be described in detail below with reference to the accompanying drawings and in conjunction with the embodiments.

Embodiment 1: Preparation of Cannabidiol According to the Following Method

The embodiment part provides the preparation of cannabidiol under different technical parameter conditions by using the methods of the present invention. The amount of the raw material adopted in each embodiment, such as industrial hemp flowers, leaves, roots, stalk cores and/or seed cakes, is respectively 10 kg, and no further explanation is given below.

1) grinding industrial hemp flowers and leaves, sifting through an 80-mesh sieve, and drying at the temperature of 60° C. for 3 h to obtain crude drug powder, of which the water content is measured to be 4%;

2) performing reflux extraction on the crude drug powder with 30% (V/V) ethanol, which is 2 times the amount of the crude drug powder, 3 times, 0.5 h each time, to obtain an extracting solution;

3) concentrating the extracting solution until the relative density is measured to be 1.05 at 50° C., thereby obtaining an extractum;

4) performing water precipitation for the extractum at the temperature of 20° C. for 1 h by using purified water which is 1 times the amount of the extractum, so as to remove impurities, thereby obtaining a water precipitation solution;

5) centrifuging the water precipitation solution at the speed of 5000 rpm, and adding 100% (V/V) ethanol to dissolve the precipitate obtained by centrifuging, thereby obtaining a precipitate alcohol solution;

6) performing column chromatography on the precipitate alcohol solution, wherein a filler of the chromatographic column is AB-8, the elution solvent is ethanol and water, and the elution includes the steps of: performing elution with 30% (V/V) ethanol for impurity removal, performing elution with 80% (V/V) ethanol to obtain a target product part, and finally, performing elution with 95% (V/V) ethanol to regenerate the chromatographic column;

7) concentrating the eluate obtained in step 6) until the relative density is 1.15 at 50° C., and adding 100% (V/V) ethanol for supersaturation and dissolution at the temperature of 10° C. to obtain a crystal;

8) adding purified water at the temperature of 0° C. to wash the crystal in step 7), thereby obtaining a primary product;

9) uniformly mixing the primary product in step 8) with purified water, and performing vacuum drying to obtain the cannabidiol; and 10) performing jet grinding on the cannabidiol obtained in step 9) to obtain the product 1.

Embodiment 2: Preparation of Cannabidiol According to the Following Method 1) grinding industrial hemp flowers and leaves, sifting through a 10-mesh sieve to obtain crude drug powder, and drying at the temperature of 200° C. for 0.5 h to obtain crude drug powder, of which the water content is measured to be 2.7%;

2) performing ultrasonic extraction on the crude drug powder with 100% (V/V) ethanol which is 2 times the amount of the crude drug powder, 1 time, 1 h each time, to obtain an extracting solution;

3) concentrating the extracting solution until the relative density is measured to be 1.35 at 50° C., thereby obtaining an extractum;

4) performing water precipitation for the extractum at the temperature of 0° C. for 48 h by using purified water which is 10 times the amount of the extractum, so as to remove impurities, thereby obtaining a water precipitation solution;

5) centrifuging the water precipitation solution at the speed of 10000 rpm, and adding 10% (V/V) ethanol to dissolve the precipitate obtained by centrifuging, thereby obtaining a precipitate alcohol solution;

6) performing column chromatography on the precipitate alcohol solution, wherein a filler of the chromatographic column is MCI resin, the elution solvent is ethanol and water, and the elution includes the steps of: performing elution with 10% (V/V) ethanol for impurity removal, performing elution with 40% (V/V) ethanol to obtain a target product part, and finally, performing elution with 90% (V/V) ethanol to regenerate the chromatographic column;

7) concentrating the eluate obtained in step 6) until the relative density is 1.25 at 50° C., and adding 60% (V/V) ethanol for supersaturation and dissolution at the temperature of 80° C. to obtain a crystal;

8) adding 5% (V/V) ethanol at the temperature of 24° C. to wash the crystal in step 7), thereby obtaining a primary product;

9) uniformly mixing the primary product in step 8) with purified water, and performing freeze drying to obtain the cannabidiol; and 10) performing cryogenic grinding on the cannabidiol obtained in step 9) to obtain the product 2.

Embodiment 3: Preparation of Cannabidiol According to the Following Method 1) grinding industrial hemp flowers and leaves, sifting through a 40-mesh sieve, and drying at the temperature of 130° C. for 1.7 h to obtain crude drug powder, of which the water content is measured to be 3.1%;

2) performing soaking extraction on the crude drug powder with 60% (V/V) ethanol which is 5 times the amount of the crude drug powder, 2 times, 2.5 h each time, to obtain an extracting solution;

3) concentrating the extracting solution until the relative density is measured to be 1.2 at 50° C., thereby obtaining an extractum;

4) performing water precipitation for the extractum at the temperature of 10° C. for 24 h by using purified water which is 5 times the amount of the extractum, so as to remove impurities, thereby obtaining a water precipitation solution;

5) centrifuging the water precipitation solution at the speed of 7500 rpm, and adding 60% (V/V) ethanol to dissolve the precipitate obtained by centrifuging, thereby obtaining a precipitate alcohol solution;

6) performing column chromatography on the precipitate alcohol solution, wherein a filler of the chromatographic column is ODS, the elution solvent is ethanol and water, and the elution includes the steps of: performing elution with 25% (V/V) ethanol for impurity removal, performing elution with 60% (V/V) ethanol to obtain a target product part, and finally, performing elution with 93% (V/V) ethanol to regenerate the chromatographic column;

7) concentrating the eluate obtained in step 6) until the relative density is measured to be 1.2 at 50° C., and adding 80% (V/V) ethanol for supersaturation and dissolution at the temperature of 45° C. to obtain a crystal;

8) adding 40% (V/V) ethanol at the temperature of 12° C. to wash the crystal in step 7), thereby obtaining a primary product;

9) performing vacuum drying on the primary product in step 8) to obtain the cannabidiol; and 10) performing jet grinding on the cannabidiol obtained in step 9) to obtain the product 3.

Embodiment 4: Preparation of Cannabidiol According to the Following Method 1) grinding industrial hemp flowers and leaves, sifting through a 40-mesh sieve, and drying at the temperature of 120° C. for 1 h to obtain crude drug powder, of which the water content is measured to be 2.6%;

2) performing ultrasonic extraction on the crude drug powder with 70% (V/V) ethanol which is 3 times the amount of the crude drug powder, under the frequency of 60 Hz, 3 times, 0.5 h each time, to obtain an extracting solution;

3) concentrating the extracting solution until the relative density is 1.1 at 50° C., thereby obtaining an extractum;

4) performing water precipitation for the extractum at the temperature of 4° C. for 12 h by using purified water which is 5 times the amount of the extractum, so as to remove impurities, thereby obtaining a water precipitation solution;

5) centrifuging the water precipitation solution at the speed of 5000 rpm, and adding 80% (V/V) ethanol to dissolve the precipitate obtained by centrifuging, thereby obtaining a precipitate alcohol solution;

6) performing column chromatography on the precipitate alcohol solution, wherein a filler of the chromatographic column is MCI resin, the elution solvent is ethanol and water, and the elution includes the steps of: performing elution with 15% (V/V) ethanol for impurity removal, performing elution with 75% (V/V) ethanol to obtain a target product part, and finally, performing elution with 95% (V/V) ethanol to regenerate the chromatographic column;

7) concentrating the eluate obtained in step 6) until the relative density is 1.1 at 50° C., and adding 80% (V/V) ethanol for supersaturation and dissolution at the temperature of 70° C. to obtain a crystal;

8) adding 10% (V/V) ethanol at the temperature of 10° C. to elute the crystal in step 7), thereby obtaining a primary product;

9) performing vacuum drying on the primary product in step 8) to obtain the cannabidiol; and 10) performing jet grinding on the cannabidiol obtained in step 9) to obtain the product 4.

Embodiment 5: Preparation of Cannabidiol According to the Following Method 1) grinding industrial hemp flowers and leaves, sifting through a 40-mesh sieve, and drying at the temperature of 120° C. for 1 h to obtain crude drug powder, of which the water content is measured to be 2.6%;

2) performing ultrasonic extraction on the crude drug powder with 80% (V/V) ethanol, which is 5 times the amount of the crude drug powder, under the frequency of 70 Hz, 2 times, 0.5 h each time, to obtain an extracting solution;

3) concentrating the extracting solution until the relative density is 1.1 at 50° C., thereby obtaining an extractum;

4) performing water precipitation for the extractum at the temperature of 4° C. for 12 h by using purified water which is 5 times the amount of the extractum, thereby obtaining a water precipitation solution;

5) centrifuging the water precipitation solution at the speed of 5000 rpm, and adding 80% (V/V) ethanol to dissolve the precipitate obtained by centrifuging, thereby obtaining a precipitate alcohol solution;

6) performing column chromatography on the precipitate alcohol solution, wherein a filler of the chromatographic column is MCI resin, the elution solvent is ethanol and water, and the elution includes the steps of: performing elution with 30% (V/V) ethanol for impurity removal, performing elution with 75% (V/V) ethanol to obtain a target product part, and finally, performing elution with 95% (V/V) ethanol to regenerate the chromatographic column;

7) concentrating the eluate obtained in step 6) until the relative density is 1.1 at 50° C., and adding 80% (V/V) ethanol for supersaturation and dissolution at the temperature of 70° C. to obtain a crystal;

8) adding 10% (V/V) ethanol at the temperature of 10° C. to wash the crystal in step 7), thereby obtaining a primary product;

9) performing vacuum drying on the primary product in step 8) to obtain the cannabidiol; and 10) performing jet grinding on the cannabidiol obtained in step 9) to obtain the product 5.

Embodiment 6: Preparation of Cannabidiol According to the Following Method 1) grinding industrial hemp flowers and leaves, sifting through a 40-mesh sieve, and drying at the temperature of 120° C. for 1 h to obtain crude drug powder, of which the water content is measured to be 2.6%;

2) performing reflux extraction on the crude drug powder with 80% (V/V) ethanol, which is 5 times the amount of the crude drug powder, 2 times, 1.5 h each time, to obtain an extracting solution;

3) concentrating the extracting solution until the relative density is 1.1 at 50° C., thereby obtaining an extractum;

4) performing water precipitation for the extractum at the temperature of 4° C. for 12 h by using purified water which is 5 times the amount of the extractum, thereby obtaining a water precipitation solution;

5) centrifuging the water precipitation solution at the speed of 5000 rpm, and adding 80% (V/V) ethanol to dissolve the precipitate obtained by centrifuging, thereby obtaining a precipitate alcohol solution;

6) performing column chromatography on the precipitate alcohol solution, wherein a filler of the chromatographic column is MCI resin, the elution solvent is ethanol and water, and the elution includes the steps of: performing elution with 30% (V/V) ethanol for impurity removal, performing elution with 75% (V/V) ethanol to obtain a target product part, and finally, performing elution with 95% (V/V) ethanol to regenerate the chromatographic column;

7) concentrating the eluate obtained in step 6) until the relative density is 1.1 at 50° C., and adding 80% (V/V) ethanol for supersaturation and dissolution at the temperature of 70° C. to obtain a crystal;

8) adding 10% (V/V) ethanol at the temperature of 10° C. to wash the crystal in step 7), thereby obtaining a primary product;

9) performing vacuum drying on the primary product in step 8) to obtain the cannabidiol; and 10) performing jet grinding on the cannabidiol obtained in step 9) to obtain the product 6.

Embodiment 7: Preparation of Cannabidiol According to the Following Method 1) grinding industrial hemp flowers and leaves, sifting through a 40-mesh sieve, and drying at the temperature of 120° C. for 1 h to obtain crude drug powder, of which the water content is measured to be 2.6%;

2) performing soaking extraction on the crude drug powder with 80% (V/V) ethanol which is 5 times the amount of the crude drug powder, 2 times, 2.5 h each time, to obtain an extracting solution;

3) concentrating the extracting solution until the relative density is 1.1 at 50° C., thereby obtaining an extractum;

4) performing water precipitation for the extractum at the temperature of 4° C. for 12 h by using purified water which is 5 times the amount of the extractum, thereby obtaining a water precipitation solution;

5) centrifuging the water precipitation solution at the speed of 5000 rpm, and adding 80% (V/V) ethanol to dissolve the precipitate obtained by centrifuging, thereby obtaining a precipitate alcohol solution;

6) performing column chromatography on the precipitate alcohol solution, wherein a filler of the chromatographic column is MCI resin, the elution solvent is ethanol and water, and the elution includes the steps of: performing elution with 30% (V/V) ethanol for impurity removal, performing elution with 75% (V/V) ethanol to obtain a target product part, and finally, performing elution with 95% (V/V) ethanol to regenerate the chromatographic column;

7) concentrating the eluate obtained in step 6) until the relative density is 1.1 at 50° C., and adding 80% (V/V) ethanol for supersaturation and dissolution at the temperature of 70° C. to obtain a crystal;

8) adding 10% (V/V) ethanol at the temperature of 10° C. to elute the crystal in step 7), thereby obtaining a primary product;

9) performing vacuum drying on the primary product in step 8) to obtain the cannabidiol; and 10) performing jet grinding on the cannabidiol obtained in step 9) to obtain the product 7.

Embodiment 8: Preparation of Cannabidiol According to the Following Method 1) grinding industrial hemp roots, sifting through a 10-mesh sieve, and drying at the temperature of 120° C. for 1 h to obtain crude drug powder, of which the water content is measured to be 1.2%;

2) performing soaking extraction on the crude drug powder with 80% (V/V) ethanol, which is 8 times the amount of the crude drug powder, 2 times, 3 h each time, to obtain an extracting solution;

3) concentrating the extracting solution until the relative density is 1.1 at 50° C., thereby obtaining an extractum;

4) performing water precipitation for the extractum at the temperature of 4° C. for 24 h by using purified water which is 10 times the amount of the extractum, thereby obtaining a water precipitation solution;

5) centrifuging the water precipitation solution at the speed of 5000 rpm, and adding 80% (V/V) ethanol to dissolve the precipitate obtained by centrifuging, thereby obtaining a precipitate alcohol solution;

6) performing column chromatography on the precipitate alcohol solution, wherein a filler of the chromatographic column is MCI resin, the elution solvent is ethanol and water, and the elution includes the steps of: performing elution with 30% (V/V) ethanol for impurity removal, performing elution with 75% (V/V) ethanol to obtain a target product part, and finally, performing elution with 95% (V/V) ethanol to regenerate the chromatographic column;

7) concentrating the eluate obtained in step 6) until the relative density is 1.1 at 50° C., and adding 80% (V/V) ethanol for supersaturation and dissolution at the temperature of 70° C. to obtain a crystal;

8) adding 10% (V/V) ethanol at the temperature of 10° C. to elute the crystal in step 7), thereby obtaining a primary product;

9) performing vacuum drying on the primary product in step 8) to obtain the cannabidiol; and 10) performing jet grinding on the cannabidiol obtained in step 9) to obtain the product 8.

Embodiment 9: Preparation of Cannabidiol According to the Following Method 1) grinding industrial hemp stalk cores, sifting through a 40-mesh sieve, and drying at the temperature of 120° C. for 1 h to obtain crude drug powder, of which the water content is measured to be 1.8%;

2) performing reflux extraction on the crude drug powder with 80% (V/V) ethanol, which is 5 times the amount of the crude drug powder, 2 times, 1.5 h each time, to obtain an extracting solution;

3) concentrating the extracting solution until the relative density is 1.1 at 50° C., thereby obtaining an extractum;

4) performing water precipitation for the extractum at the temperature of 4° C. for 12 h by using purified water which is 5 times the amount of the extractum, thereby obtaining a water precipitation solution;

5) centrifuging the water precipitation solution at the speed of 5000 rpm, and adding 80% (V/V) ethanol to dissolve the precipitate obtained by centrifuging, thereby obtaining a precipitate alcohol solution;

6) performing column chromatography on the precipitate alcohol solution, wherein a filler of the chromatographic column is MCI resin, the elution solvent is ethanol and water, and the elution includes the steps of: performing elution with 30% (V/V) ethanol for impurity removal, performing elution with 75% (V/V) ethanol to obtain a target product part, and finally, performing elution with 95% (V/V) ethanol to regenerate the chromatographic column;

7) concentrating the eluate obtained in step 6) until the relative density is 1.1 at 50° C., and adding 80% (V/V) ethanol for supersaturation and dissolution at the temperature of 70° C. to obtain a crystal;

8) adding 10% (V/V) ethanol at the temperature of 10° C. to wash the crystal in step 7), thereby obtaining a primary product;

9) performing vacuum drying on the primary product in step 8) to obtain the cannabidiol; and 10) performing jet grinding on the cannabidiol obtained in step 9) to obtain the product 9.

Embodiment 10: Preparation of Cannabidiol According to the Following Method 1) grinding industrial hemp flowers, leaves and seed cakes, sifting through a 10-mesh sieve, and drying at the temperature of 200° C. for 0.5 h to obtain crude drug powder, of which the water content is measured to be 2.4%;

2) performing ultrasonic extraction on the crude drug powder with 100% (V/V) ethanol, which is 2 times the amount of the crude drug powder, 1 time, 1 h each time, to obtain an extracting solution;

3) concentrating the extracting solution until the relative density is measured to be 1.35 at 50° C., thereby obtaining an extractum;

4) performing water precipitation for the extractum at the temperature of 0° C. for 48 h by using purified water which is 10 times the amount of the extractum, so as to remove impurities, thereby obtaining a water precipitation solution;

5) centrifuging the water precipitation solution at the speed of 10000 rpm, and adding 10% (V/V) ethanol to dissolve the precipitate obtained by centrifuging, thereby obtaining a precipitate alcohol solution;

6) performing column chromatography on the precipitate alcohol solution, wherein a filler of the chromatographic column is MCI resin, the elution solvent is ethanol and water, and the elution includes the steps of: performing elution with 10% (V/V) ethanol for impurity removal, performing elution with 40% (V/V) ethanol to obtain a target product part, and finally, performing elution with 90% (V/V) ethanol to regenerate the chromatographic column;

7) concentrating the eluate obtained in step 6) until the relative density is 1.25 at 50° C., and adding 60% (V/V) ethanol for supersaturation and dissolution at the temperature of 80° C. to obtain a crystal;

8) adding 5% (V/V) ethanol at the temperature of 24° C. to wash the crystal in step 7), thereby obtaining a primary product;

9) uniformly mixing the primary product in step 8) with purified water, and performing freeze drying to obtain the cannabidiol; and 10) performing cryogenic grinding on the cannabidiol obtained in step 9) to obtain the product 10.

Comparative Embodiment 1: Preparation of Cannabidiol According to the Following Method 1) adding flowers and leaves in the full-bloom stage into a drying plant, and drying at 130° C. for 35 mM;

2) grinding the dried flowers and leaves until the particle size reaches 5-10 meshes;

3) soaking the ground flowers and leaves in a soaking device, wherein the soaking solvent is petroleum ether, the soaking temperature is 48° C., and the soaking time length is 1 h;

4) after the soaking, filtering out the flowers and leaves, and heating the filtrate at 90° C. to obtain an extractum; and 5) chromatographic separation: weighing an adsorbent, adding the adsorbent into a chromatographic separator, uniformly putting the extractum on the adsorbent surface to adsorb CBD (the weight ratio of the adsorbent to the extractum is 25:1), performing elution by using petroleum ether, and drying to obtain the comparative product 1.

Comparative Embodiment 2: Preparation of Cannabidiol According to the Following Method 1) adding hemp flowers and leaves in the full-bloom stage into a drying plant, and drying at 160° C. for 15 min;

2) grinding the dried flowers and leaves until the particle size reaches 5-10 meshes;

3) soaking the ground flowers and leaves in a soaking device, wherein the soaking solvent is n-hexane, the soaking temperature is 20° C., and the soaking time length is 2 h;

4) after the soaking, filtering out the flowers and leaves, and heating the filtrate at 120° C. to obtain an extractum; and 5) chromatographic separation: weighing an adsorbent macroporous resin, adding the adsorbent macroporous resin into a chromatographic separator, uniformly mixing the adsorbent and the extractum in a ratio of 1:1 to adsorb CBD, performing elution by using n-hexane, and drying to obtain the comparative product 2.

Experimental Embodiment 1: Comparison of CBD Content and Tetrahydrocannabinol Detection Results in Products Obtained by Different Preparation Methods Detection Method:

Chromatographic Condition and System Suitability Test:

octadecyl silane bonded silica gel is used as a filler; isocratic elution is performed by using acetonitrile as a mobile phase A and water as a mobile phase B according to A (%):B (%)=80:20; and the detection wavelength is 210 nm. The number of theoretical plates calculated according to the CBD peak should be not lower than 2500.

Preparation of Reference Substance Solutions:

precisely weighing a CBD reference substance, and adding methanol (1:1) to prepare a reference substance solution, every 1 ml of which contains 0.1 mg of the CBD reference substance; and precisely weighing a tetrahydrocannabinol reference substance, and adding methanol (1:1) to prepare a reference substance solution, every 1 ml of which contains 0.01 mg of the tetrahydrocannabinol reference substance.

Preparation of Test Sample Solution:

taking about 25 mg of the product which is precisely weighed, putting the product in a 25 ml measuring flask, adding 20 ml of acetonitrile-water (1:1), performing ultrasonic treatment for 15 minutes, adding acetonitrile-water (1:1) for dilution to the calibration, shaking uniformly, performing filtration through a microporous filter membrane (0.45 μm), and taking the subsequent filtrate.

Determination Method:

respectively precisely sucking 10 μl of the reference substance solution and 10 μl of the test sample solution, injecting the reference substance solution and test sample solution into a liquid chromatograph, and performing determination.

The CBD content and tetrahydrocannabinol content detection results of the products prepared according to the embodiments 1-7 and comparative embodiments 1-2 are referred to Table 1 and FIG. 1 to FIG. 9.

TABLE 1

Comparison of CBD content and THC detection results in products obtained by different preparation methods

Figure 2:
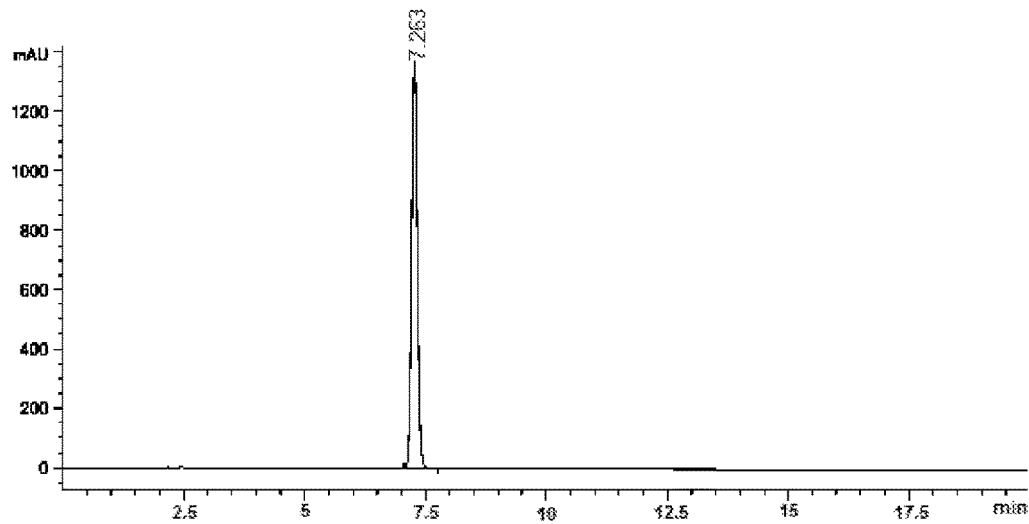
FIG. 2 shows a chromatogram of the product 2.
Figure 3:
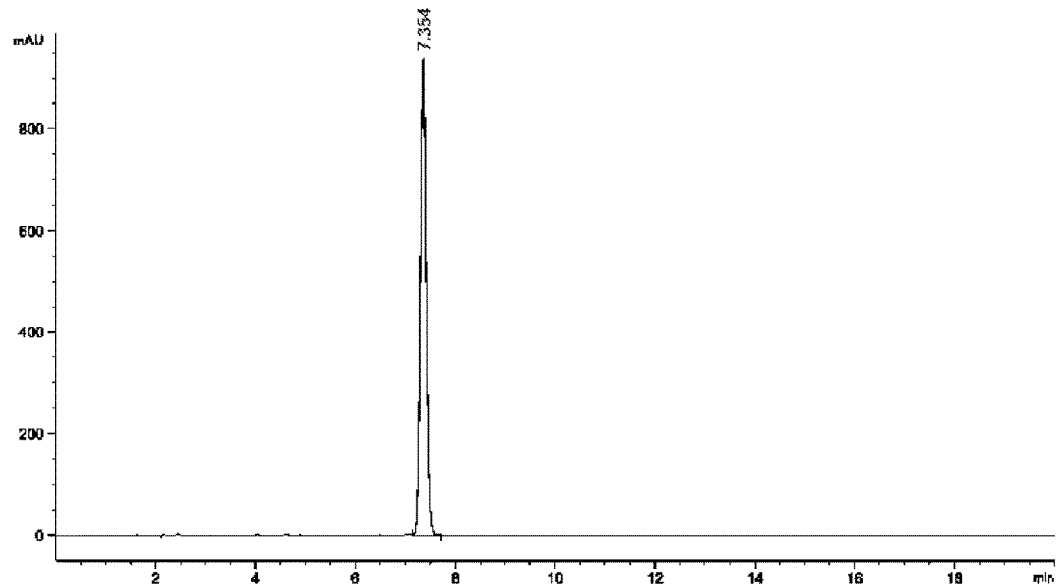
FIG. 3 shows a chromatogram of the product 3.
Figure 4:
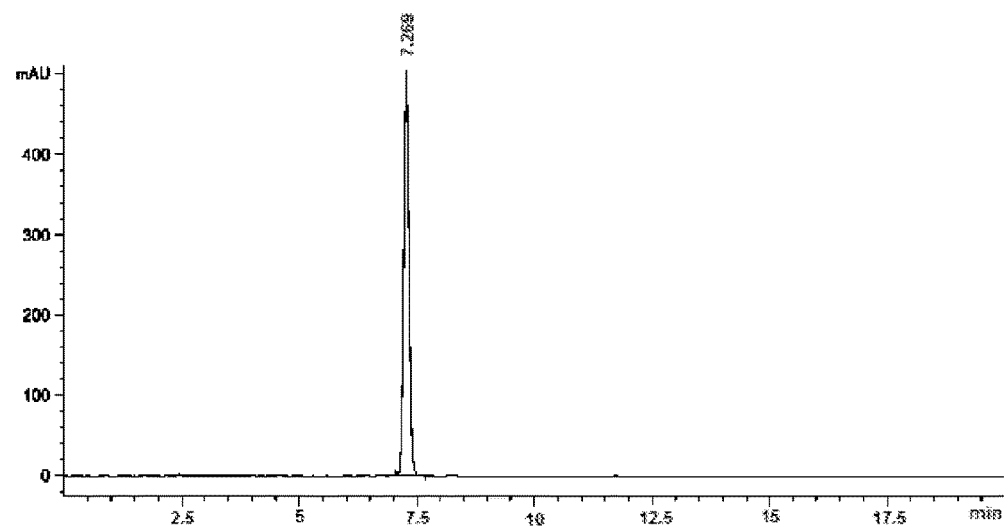
FIG. 4 shows a chromatogram of the product 4.
Figure 5:
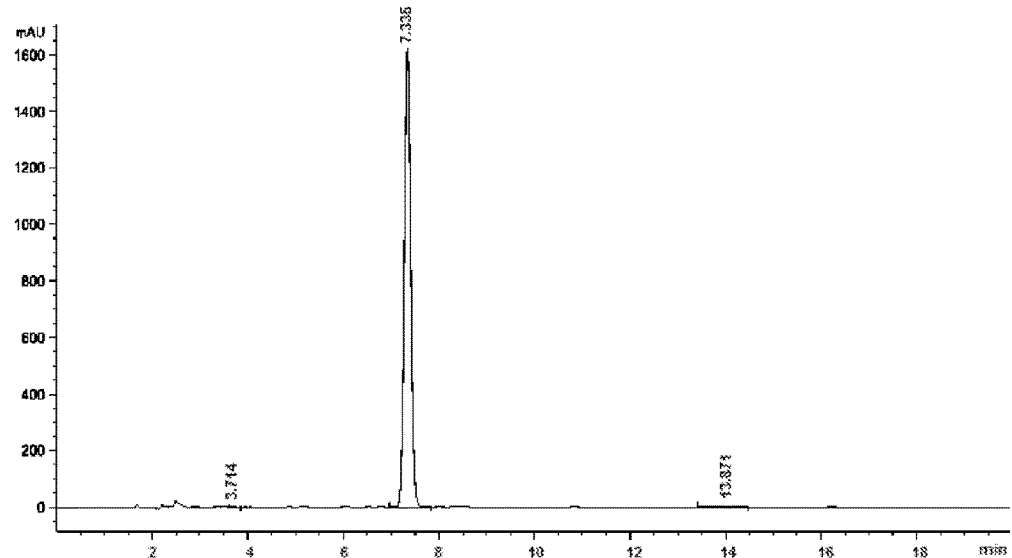
FIG. 5 shows a chromatogram of the product 5.
Figure 6:
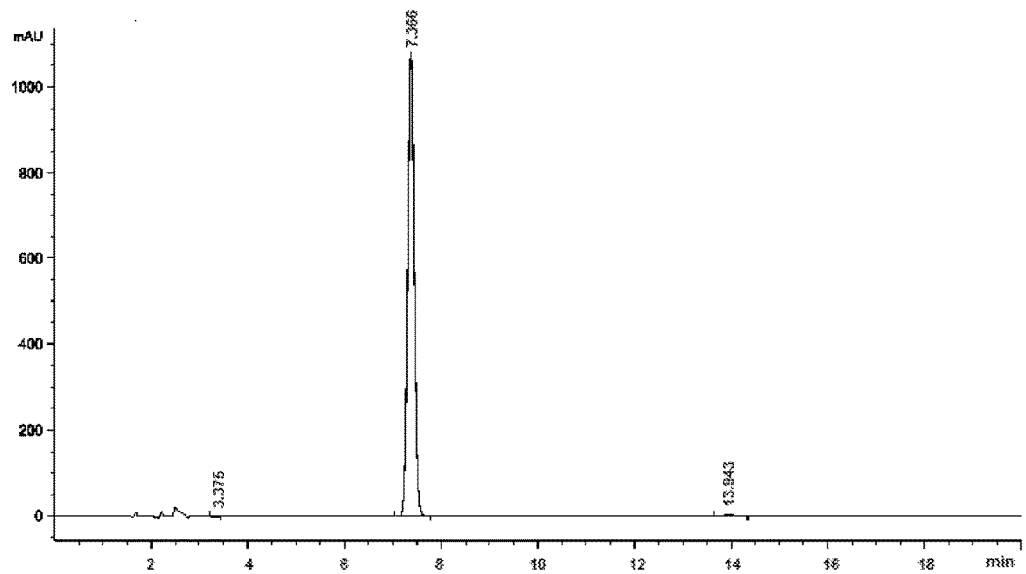
FIG. 6 shows a chromatogram of the product 6.
Figure 7:
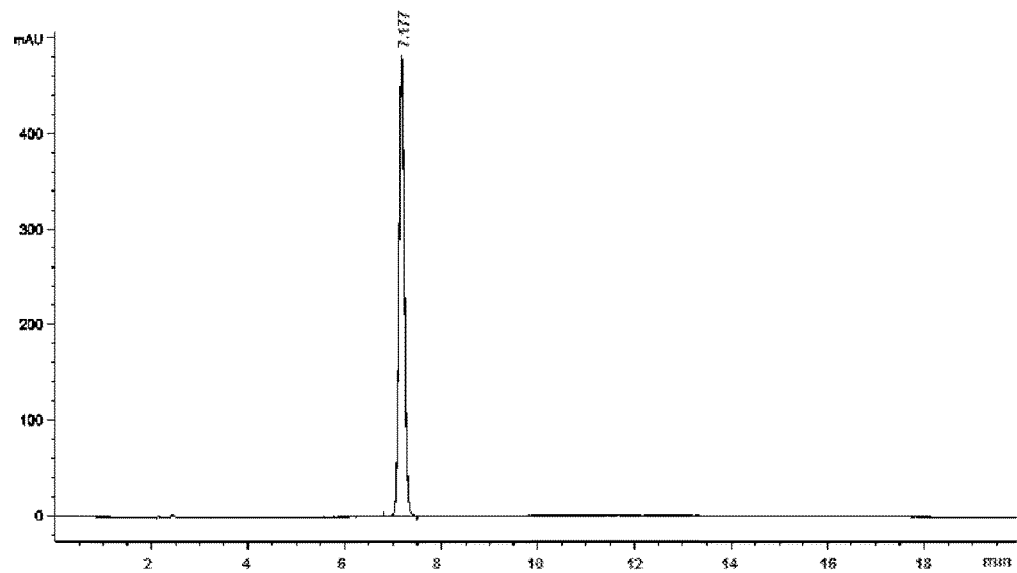
FIG. 7 shows a chromatogram of the product 7.
Figure 8:
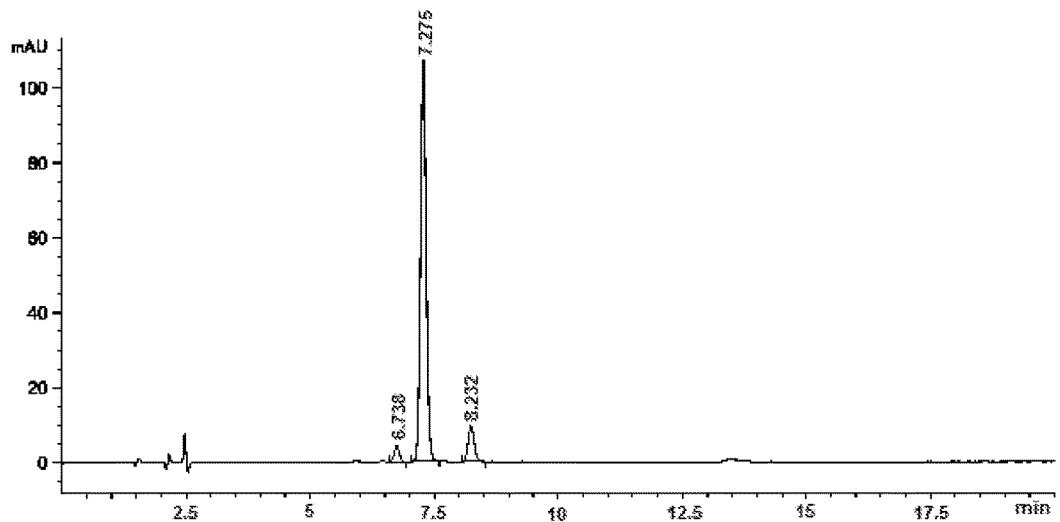
FIG. 8 shows a chromatogram of the comparative product 1.
Figure 9:
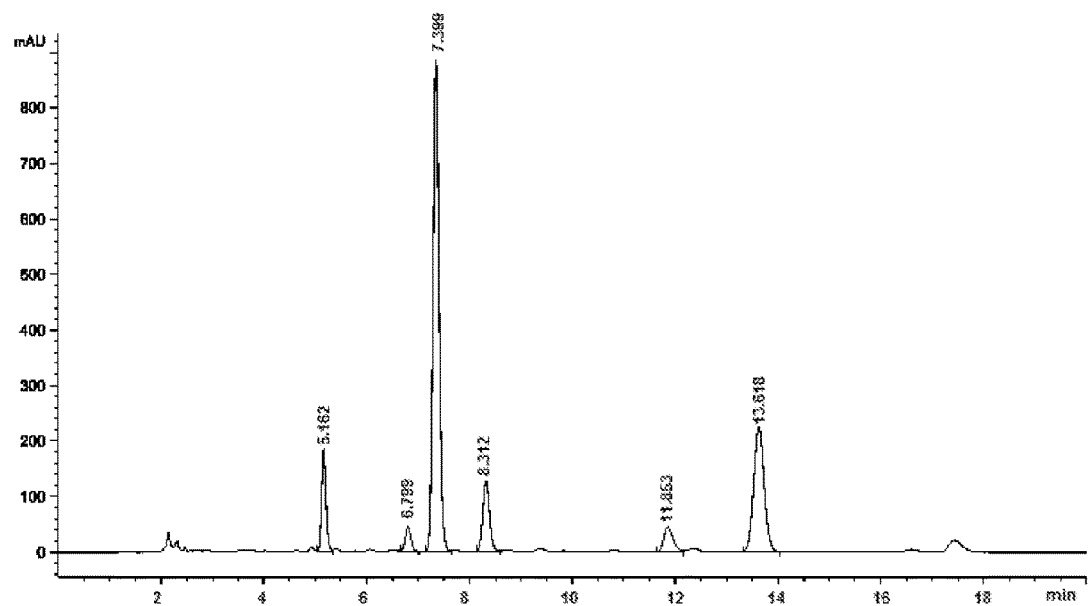
FIG. 9 shows a chromatogram of the comparative product 2.

| Product Name | Chromatogram | CBD Content (wt %) | THC Content (wt %) |
| --- | --- | --- | --- |
| Product 1 | FIG. 1 | 97.4 | ND |
| Product 2 | FIG. 2 | 96.3 | ND |
| Product 3 | FIG. 3 | 98.5 | ND |
| Product 4 | FIG. 4 | 98.9 | ND |
| Product 5 | FIG. 5 | 98.5 | ND |
| Product 6 | FIG. 6 | 97.4 | ND |
| Product 7 | FIG. 7 | 99.5 | ND |
| Comparative Product 1 | FIG. 8 | 83.1 | 0.11 |
| Comparative Product 2 | FIG. 9 | 81.2 | 0.24 |

It can be seen from Table 1 and FIG. 1 to FIG. 9 that the contents of CBD (cannabidiol) in the products 1, 2, 3, 4, 5, 6 and 7 prepared by the methods of the present invention are obviously higher than the contents of CBD (comparative product 1 and comparative product 2) prepared by the prior art; and no THC (tetrahydrocannabinol) is detected in the products prepared by the techniques of the present invention, but THC is obviously detected in the products prepared by the prior art, which further illustrates that the CBD extracted by using the present invention has higher content, higher purity and higher safety and complies with related requirements of laws and regulations on products.

Experimental Embodiment 2: Comparison of Effects of Different Extraction Methods on CBD Extraction Rate (1) Raw Flower and Leaf Crude Drug Content Detection Method Chromatographic Condition and System Suitability Test:

octadecyl silane bonded silica gel is used as a filler; isocratic elution is performed by using acetonitrile as a mobile phase A and water as a mobile phase B according to A (%):B (%)=80:20; and the detection wavelength is 210 nm. The number of theoretical plates calculated according to the CBD peak should be not lower than 2500.

Preparation of Reference Substance Solutions:

precisely weighing a CBD reference substance, and adding methanol (1:1) to prepare a reference substance solution, every 1 ml of which contains 0.1 mg of the CBD reference substance; and precisely weighing a tetrahydrocannabinol reference substance, and adding methanol (1:1) to prepare a reference substance solution, every 1 ml of which contains 0.01 mg of the tetrahydrocannabinol reference substance.

Preparation of Test Sample Solution:

taking about 1 g of the product which is precisely weighed, adding 25 ml of methanol, performing ultrasonic treatment for 15 minutes, performing filtration, adding 25 ml of methanol, performing ultrasonic treatment for 15 minutes, combining the filtrates, making up to 50 ml, shaking uniformly, performing filtration through a microporous filter membrane (0.45 μm), and taking the subsequent filtrate.

Determination Method:

respectively precisely sucking 10 μl of the reference substance solution and 10 μl of the test sample solution, injecting the reference substance solution and test sample solution into a liquid chromatograph, and performing determination.

(2) Extracting Solution Content Detection Method

Chromatographic Condition and System Suitability Test:

octadecyl silane bonded silica gel is used as a filler; isocratic elution is performed by using acetonitrile as a mobile phase A and water as a mobile phase B according to A (%):B (%)=80:20; and the detection wavelength is 210 nm. The number of theoretical plates calculated according to the CBD peak should be not lower than 2500.

Preparation of Reference Substance Solutions:

precisely weighing a CBD reference substance, and adding methanol (1:1) to prepare a reference substance solution, every 1 ml of which contains 0.1 mg of the CBD reference substance; and precisely weighing a tetrahydrocannabinol reference substance, and adding methanol (1:1) to prepare a reference substance solution, every 1 ml of which contains 0.01 mg of the tetrahydrocannabinol reference substance.

Preparation of Test Sample Solution:

taking 1 ml of the extracting solution, making up to 25 ml, performing filtration through a microporous filter membrane (0.45 μm), and taking the subsequent filtrate.

Determination Method:

respectively precisely sucking 10 μl of the reference substance solution and 10 μl of the test sample solution, injecting the reference substance solution and test sample solution into a liquid chromatograph, and performing determination.

The three methods in the embodiments 5-7, namely ultrasonic extraction, reflux extraction and soaking extraction, are adopted to obtain the extracting solution in step (2) as the test sample solution. Specific experimental results of the extraction rate are shown in Table 2 below.

TABLE 2

Extraction rate tests of three extraction methods (using CBD content as an index)

|  | Flower and Leave Crude Drug | Ultrasonic Extraction (Embodiment 5) | Reflux Extraction (Embodiment 6) | Soaking Extraction (Embodiment 7) |
|---|---|---|---|---|
| Weight or Volume | 10 kg | 92.6 L | 91.8 L | 92.7 L |
| CBD Content | 49.8 g | 48.1 g | 48.0 g | 48.2 g |
| Extraction Rate % | — | 96.6 | 96.3 | 96.8 |

From Table 2 above, it can be seen that the extraction rates of the three extraction methods are similar, and the change of the extraction method has no effect on the extraction rate. Under the condition that other technical parameters are identical, there was no significant difference between the content of CBD (cannabidiol) in the product 7 obtained by soaking extraction and the content of CBD (cannabidiol) in the product 5 obtained by ultrasonic extraction, which further illustrates that the beneficial effects of the present invention are not due to the introduction of the ultrasonic extraction technique.

Experimental Embodiment 3: Comparison of CBD Content and Tetrahydrocannabinol Detection Results in Products Prepared from Different Extraction Parts The detection method is the same as that of the experimental embodiment 1. The CBD content and tetrahydrocannabinol content detection results of the products prepared in the embodiments 8-10 are referred to Table 3.

TABLE 3

Comparison of CBD content and THC detection results in products prepared from different extraction parts

| Product Name | CBD Content (wt %) | THC Content (wt %) |
|---|---|---|
| Product 8 | 95.3 | ND |
| Product 9 | 94.8 | ND |
| Product 10 | 95.2 | ND |

From Table 3, it can be seen that the method of the present invention is also suitable for performing extraction on hemp roots, stalk cores, flowers, leaves and seed cakes to obtain CBD, and no THC (tetrahydrocannabinol) is detected in the products.

Experimental Embodiment 4: Detection of Stability of Products Prepared by Different Preparation Methods by Using Stability Test Methods Main Instruments:

Drug stability test chamber (long-term): SHH-250SD, Chongqing Yongsheng Experiment Instrument Factory;

Drug stability test chamber (accelerated): SHH-250SD, Chongqing Yongsheng Experiment Instrument Factory;

HPLC: Agilent1200;

Analytical balance: MS-105DU, METTLER TOLEDO in Switzerland;

Ultraviolet-visible spectrophotometer: UV-2550, SHIMADZU in Japan

TLC Visualizer: TLC Visualizer, CAMAG in Switzerland;

Test Samples:

Accelerated stability tests are performed on the samples prepared according to the methods of the above-mentioned embodiments and comparative embodiments, and the test results are shown in Tables 4 to 12.

TABLE 4

Product 1 stability test

| | | | Time Point: | | | | |
|---|---|---|---|---|---|---|---|
| | | | Beginning | 1st Month | 2nd Month | 3rd Month | 6th Month |
| | | | Date of Sampling: | | | | |
| Test Item: | Test Method: | Acceptance Criteria | 2015 Nov. 3 | 2015 Dec. 3 | 2016 Jan. 3 | 2016 Feb. 3 | 2016 May 3 |
| | | | Detection Results | | | | |
| Trait | Visual | White, light yellow powder or crystal | Acceptable | Acceptable | Acceptable | Acceptable | Acceptable |

TABLE 4-continued

Product 1 stability test

| Test Item: | Test Method: | Acceptance Criteria | Beginning 2015 Nov. 3 | 1st Month 2015 Dec. 3 | 2nd Month 2016 Jan. 3 | 3rd Month 2016 Feb. 3 | 6th Month 2016 May 3 |
|---|---|---|---|---|---|---|---|
| Identification | TLC | The chromatogram of the test sample and the chromatogram of the reference substance show the fluorescent spots of the same color in the corresponding positions. | Acceptable | Acceptable | Acceptable | Acceptable | Acceptable |
| Content Determination | HPLC | CBD content ≥95% | 97.4 | 97.6 | 97.2 | 97.7 | 97.5 |
|  | HPLC | THC content ≤0.1% | ND | ND | ND | ND | ND |
| Microbe | Microbial Detection Method in Chinese Pharmacopoeia | Bacterial count does not exceed 1000 cfu/g | <10 | ND | ND | ND | <10 |
|  |  | Fungal and yeast count does not exceed 100 cfu/g | <10 | ND | ND | ND | <10 |
|  |  | No *E. coli* should be detected | ND | ND | ND | ND | ND |

TABLE 5

Product 2 stability test

| Test Item: | Test Method: | Acceptance Criteria: | Beginning 2015 Nov. 3 | 1st Month 2015 Dec. 3 | 2nd Month 2016 Jan. 3 | 3rd Month 2016 Feb. 3 | 6th Month 2016 May 3 |
|---|---|---|---|---|---|---|---|
| Trait | Visual | White, light yellow powder or crystal | Acceptable | Acceptable | Acceptable | Acceptable | Acceptable |
| Identification | TLC | The chromatogram of the test sample and the chromatogram of the reference substance show the fluorescent spots of the same color in the corresponding positions. | Acceptable | Acceptable | Acceptable | Acceptable | Acceptable |
| Content Determination | HPLC | CBD content ≥95% | 96.3 | 96.6 | 96.4 | 96.7 | 96.2 |
|  | HPLC | THC content ≤0.1% | ND | ND | ND | ND | ND |
| Microbe | Microbial Detection Method in Chinese Pharmacopoeia | Bacterial count does not exceed 1000 cfu/g | <10 | ND | ND | ND | <10 |
|  |  | Fungal and yeast count does not exceed 100 cfu/g | <10 | ND | ND | ND | <10 |
|  |  | No *E. coli* should be detected | ND | ND | ND | ND | ND |

TABLE 6

Product 3 stability test

| Test Item: | Test Method: | Acceptance Criteria: | Beginning 2015 Nov. 8 | 1st Month 2015 Dec. 8 | 2nd Month 2016 Jan. 8 | 3rd Month 2016 Feb. 8 | 6th Month 2016 May 8 |
|---|---|---|---|---|---|---|---|
| Trait | Visual | White, light yellow powder or crystal | Acceptable | Acceptable | Acceptable | Acceptable | Acceptable |
| Identification | TLC | The chromatogram of the test sample and the chromatogram of the reference substance show the fluorescent spots of the same color in the corresponding positions. | Acceptable | Acceptable | Acceptable | Acceptable | Acceptable |
| Content Determination | HPLC | CBD content ≥95% | 98.5 | 98.6 | 98.7 | 98.2 | 98.8 |
| | HPLC | THC content ≤0.1% | ND | ND | ND | ND | ND |
| Microbe | Microbial Detection Method in Chinese Pharmacopoeia | Bacterial count does not exceed 1000 cfu/g | <10 | ND | ND | ND | <10 |
| | | Fungal and yeast count does not exceed 100 cfu/g | <10 | ND | ND | ND | <10 |
| | | No *E. coli* should be detected | ND | ND | ND | ND | ND |

TABLE 7

Product 4 stability test

| Test Item: | Test Method: | Acceptance Criteria: | Beginning 2015 Nov. 8 | 1st Month 2015 Dec. 8 | 2nd Month 2016 Jan. 8 | 3rd Month 2016 Feb. 8 | 6th Month 2016 May 8 |
|---|---|---|---|---|---|---|---|
| Trait | Visual | White, light yellow powder or crystal | Acceptable | Acceptable | Acceptable | Acceptable | Acceptable |
| Identification | TLC | The chromatogram of the test sample and the chromatogram of the reference substance show the fluorescent spots of the same color in the corresponding positions. | Acceptable | Acceptable | Acceptable | Acceptable | Acceptable |
| Content Determination | HPLC | CBD content ≥95% | 98.9 | 98.7 | 98.4 | 98.3 | 98.6 |
| | HPLC | THC content ≤0.1% | ND | ND | ND | ND | ND |
| Microbe | Microbial Detection Method in Chinese Pharmacopoeia | Bacterial count does not exceed 1000 cfu/g | <10 | ND | ND | ND | <10 |
| | | Fungal and yeast count does not exceed 100 cfu/g | <10 | ND | ND | ND | <10 |
| | | No *E. coli* should be detected | ND | ND | ND | ND | ND |

TABLE 8

Product 5 stability test

| Test Item: | Test Method: | Acceptance Criteria: | Beginning 2015 Nov. 8 | 1st Month 2015 Dec. 8 | 2nd Month 2016 Jan. 8 | 3rd Month 2016 Feb. 8 | 6th Month 2016 May 8 |
|---|---|---|---|---|---|---|---|
| Trait | Visual | White, light yellow powder or crystal | Acceptable | Acceptable | Acceptable | Acceptable | Acceptable |
| Identification | TLC | The chromatogram of the test sample and the chromatogram of the reference substance show the fluorescent spots of the same color in the corresponding positions. | Acceptable | Acceptable | Acceptable | Acceptable | Acceptable |
| Content Determination | HPLC | CBD content ≥95% | 98.5 | 98.4 | 98.9 | 98.5 | 98.4 |
| | HPLC | THC content ≤0.1% | ND | ND | ND | ND | ND |
| Microbe | Microbial Detection Method in Chinese Pharmacopoeia | Bacterial count does not exceed 1000 cfu/g | <10 | ND | ND | ND | <10 |
| | | Fungal and yeast count does not exceed 100 cfu/g | <10 | ND | ND | ND | <10 |
| | | No *E. coli* should be detected | ND | ND | ND | ND | ND |

TABLE 9

Product 6 stability test

| Test Item: | Test Method: | Acceptance Criteria: | Beginning 2015 Nov. 8 | 1st Month 2015 Dec. 8 | 2nd Month 2016 Jan. 8 | 3rd Month 2016 Feb. 8 | 6th Month 2016 May 8 |
|---|---|---|---|---|---|---|---|
| Trait | Visual | White, light yellow powder or crystal | Acceptable | Acceptable | Acceptable | Acceptable | Acceptable |
| Identification | TLC | The chromatogram of the test sample and the chromatogram of the reference substance show the fluorescent spots of the same color in the corresponding positions. | Acceptable | Acceptable | Acceptable | Acceptable | Acceptable |
| Content Determination | HPLC | CBD content ≥95% | 97.4 | 97.2 | 97.8 | 97.5 | 97.4 |
| | HPLC | THC content ≤0.1% | ND | ND | ND | ND | ND |
| Microbe | Microbial Detection Method in Chinese Pharmacopoeia | Bacterial count does not exceed 1000 cfu/g | <10 | ND | ND | ND | <10 |
| | | Fungal and yeast count does not exceed 100 cfu/g | <10 | ND | ND | ND | <10 |
| | | No *E. coli* should be detected | ND | ND | ND | ND | ND |

TABLE 10

Product 7 stability test

| Test Item: | Test Method: | Acceptance Criteria: | Beginning 2015 Nov. 8 | 1st Month 2015 Dec. 8 | 2nd Month 2016 Jan. 8 | 3rd Month 2016 Feb. 8 | 6th Month 2016 May 8 |
|---|---|---|---|---|---|---|---|
| | | | | | Detection Results | | |
| Trait | Visual | White, light yellow powder or crystal | Acceptable | Acceptable | Acceptable | Acceptable | Acceptable |
| Identification | TLC | The chromatogram of the test sample and the chromatogram of the reference substance show the fluorescent spots of the same color in the corresponding positions. | Acceptable | Acceptable | Acceptable | Acceptable | Acceptable |
| Content Determination | HPLC | CBD content ≥95% | 99.5 | 99.6 | 99.6 | 99.8 | 99.7 |
| | HPLC | THC content ≤0.1% | ND | ND | ND | ND | ND |
| Microbe | Microbial Detection Method in Chinese Pharmacopoeia | Bacterial count does not exceed 1000 cfu/g | <10 | ND | ND | ND | <10 |
| | | Fungal and yeast count does not exceed 100 cfu/g | <10 | ND | ND | ND | <10 |
| | | No *E. coli* should be detected | ND | ND | ND | ND | ND |

TABLE 11

Comparative product 1 stability test

| Test Item: | Test Method: | Acceptance Criteria: | Beginning 2015 Nov. 8 | 1st Month 2015 Dec. 8 | 2nd Month 2016 Jan. 8 | 3rd Month 2016 Feb. 8 | 6th Month 2016 May 8 |
|---|---|---|---|---|---|---|---|
| | | | | | Detection Results | | |
| Trait | Visual | White, light yellow powder or crystal | Acceptable | Acceptable | Acceptable | Acceptable | Acceptable |
| Identification | TLC | The chromatogram of the test sample and the chromatogram of the reference substance show the fluorescent spots of the same color in the corresponding positions. | Acceptable | Acceptable | Acceptable | Acceptable | Acceptable |
| Content Determination | HPLC | CBD content ≥95% | 83.1 | 82.2 | 80.1 | 76.1 | 73.8 |
| | HPLC | THC content ≤0.1% | ND | ND | ND | ND | ND |
| Microbe | Microbial Detection Method in Chinese Pharmacopoeia | Bacterial count does not exceed 1000 cfu/g | <10 | ND | ND | ND | <10 |
| | | Fungal and yeast count does not exceed 100 cfu/g | <10 | ND | ND | ND | <10 |
| | | No *E. coli* should be detected | ND | ND | ND | ND | ND |

TABLE 12

Comparative product 2 stability test

| Test Item: | Test Method: | Acceptance Criteria: | Beginning 2015 Nov. 8 | 1st Month 2015 Dec. 8 | 2nd Month 2016 Jan. 8 | 3rd Month 2016 Feb. 8 | 6th Month 2016 May 8 |
|---|---|---|---|---|---|---|---|
| | | | | | Detection Results | | |
| Trait | Visual | White, light yellow powder or crystal | Acceptable | Acceptable | Acceptable | Acceptable | Acceptable |
| Identification | TLC | The chromatogram of the test sample and the chromatogram of the reference substance show the fluorescent spots of the same color in the corresponding positions. | Acceptable | Acceptable | Acceptable | Acceptable | Acceptable |
| Content Determination | HPLC | CBD content ≥95% | 81.2 | 77.2 | 74.7 | 71.1 | 69.1 |
| | HPLC | THC content ≤0.1% | ND | ND | ND | ND | ND |
| Microbe | Microbial Detection Method in Chinese Pharmacopoeia | Bacterial count does not exceed 1000 cfu/g | <10 | ND | ND | ND | <10 |
| | | Fungal and yeast count does not exceed 100 cfu/g | <10 | ND | ND | ND | <10 |
| | | No E. coli should be detected | ND | ND | ND | ND | ND |

From Tables 4-12, it can be seen that the content of CBD (cannabidiol) in the products 1-7 prepared by the methods of Embodiment 1 to Embodiment 7 of the present invention is stable after the 6-month accelerated stability test. The content change range of CBD is only less than 0.6% (wherein the maximum change of CBD content is only 0.6% after storage of 3 months, 2 months and 1 month). However, the contents of CBD in the comparative product 1 and comparative product 2 prepared by the comparative embodiment methods are respectively decreased from 83.1% to 73.8% (the decrease rate is 9.3%) and from 81.2% to 69.1% (the decrease rate is 12.1%) after the 6-month accelerated stability test, so the stability is low; and in the 3-month stability test, the content decrease rates of the comparative product 1 and comparative product 2 are respectively 7.1% and 10.1%, so the stability is obviously lower than that of the products prepared by the methods of the present invention.

From the above description, it can be seen that the above-mentioned embodiments of the present invention achieve the following technical effects: 1) By adding the step of crystallization, the cannabidiol (CBD) content in the final product is increased to 96% or above. 2) By improving the technique, the tetrahydrocannabinol content in the finished product is controlled to 0.3% or below (tetrahydrocannabinol is not detected in embodiment 1 to embodiment 7), which complies with national laws and regulations, so that the product safety is guaranteed. 3) In the step of primary purification, the macroporous resin, MCI resin or ODS is used instead of the silica gel in the prior art, so that the filler can be recycled, thereby lowering the overall production cost, and reducing the environmental pollution caused by the waste silica gel. 4) By using the ethanol and water as the extraction solvents, the solvents are safe and have small damage to the environment and operating personnel, and the product solvent residues are greatly improved; and in the column chromatography process, ethanols with different purities are used to elute the resin column, thereby reducing the environmental pollution and the personal injuries.

In addition, laboratory-scale experimental verification and pilot scale-up verification show that the technique in the present invention can produce products with high purity (above 95%) and safety (THC content 0.3% or below).

The foregoing descriptions are merely preferred embodiments of the present invention and are not intended to limit the present invention. For those skilled in the art, the present invention may have various changes and modifications. Any modification, equivalent replacement, or improvement made within the spirit and principle of the present invention shall fall into the protection scope of the present invention. The protection scope of the present invention is defined by the appended claims, and covers the equivalent changes of the claims.

What is claimed is:

1. A method of extracting cannabidiol from hemp, comprising:
   1) performing grinding and drying on an extraction part of the hemp to obtain crude drug powder;
   2) extracting the crude drug powder with 30-100% (V/V) ethanol to obtain an extracting solution;
   3) concentrating the extracting solution to obtain an extractum;
   4) performing water precipitation on the extractum to remove impurities to obtain a water precipitation solution;
   5) centrifuging the water precipitation solution, and adding 10-100% (V/V) ethanol to dissolve the precipitate obtained by centrifuging, thereby obtaining a precipitate alcohol solution;
   6) performing column chromatography on the precipitate alcohol solution;
   7) concentrating the eluate obtained in step 6), and adding ethanol for supersaturation and dissolution to obtain a crystal;

8) adding purified water or ethanol to wash the crystal, thereby obtaining a primary product; and 9) uniformly mixing the primary product in step 8) with purified water, and drying to obtain the cannabidiol.

2. The method according to claim 1, wherein the drying after grinding the extraction part of the hemp in step 1) comprises:

drying for 0.5-3 h under the temperature condition of 60-200° C. until the water content is 5% or below.

3. The method according to claim 1, wherein the extraction part of the hemp in step 1) is ground to 10-80 meshes.

4. The method according to claim 1, wherein the extraction manner in step 2) comprises reflux extraction, ultrasonic extraction and/or soaking extraction: the reflux extraction includes: performing reflux extraction 1-3 times by using ethanol which is 2-8 times the amount of the crude drug powder, 0.5-3 h each time; the ultrasonic extraction includes: performing ultrasonic extraction 1-3 times by using ethanol which is 2-8 times the amount of the crude drug powder, 0.1-1 h each time; and the soaking extraction includes: performing soaking extraction 1-3 times by using ethanol which is 2-8 times the amount of the crude drug powder, 0.5-5 h each time.

5. The method according to claim 1, wherein the step 3) further comprises:

concentrating the extracting solution until the relative density is measured to be 1.05-1.35 at 50° C.

6. The method according to claim 1, wherein the step 4) further comprises:

performing water precipitation under the temperature condition of 0-20° C. for 1-48 h by using purified water which is 1-10 times the amount of the crude drug powder.

7. The method according to claim 1, wherein performing column chromatography on the precipitate alcohol solution in step 6) comprises:

performing gradient elution on a chromatographic column by using an elution solvent; and the step of gradient elution includes: performing impurity removal by using 0-30% (V/V) ethanol first, and performing elution by using 40-80% (V/V) ethanol.

8. The method according to claim 1, wherein the step of column chromatography, a filler used in the chromatographic column includes one or more of macroporous resin, MCI resin and octadecyl silane bonded silica gel.

9. The method according to claim 8, wherein the macroporous resin comprises:

one or more of AB-8, D-101, XDA-8, LSA-7, D-941, DM-130, ADS-17, SP-825 and HPD-600.

10. The method according to claim 1, wherein the step 7) further comprises:

performing supersaturation and dissolution by using 60-100% (V/V) ethanol under the temperature condition of 10-80° C. to obtain the crystal.

11. The method according to claim 1, wherein the step 8) further comprises:

adding purified water or 5-40% (V/V) ethanol for washing under the temperature condition of 0-24° C. to obtain the primary product.

12. The method according to claim 1, wherein the drying manner in step 9) comprises:

one or more of spray drying, vacuum drying, freeze drying, near-infrared drying and microwave drying, and the drying temperature does not exceed 65° C.

13. The method according to claim 1, wherein after step 9), the method further comprises:

the step of grinding the cannabidiol into powder, wherein the grinding manner includes jet grinding and/or cryogenic grinding, and the material temperature during grinding does not exceed 65° C.

14. The method according to claim 1, wherein the extraction part in step 1) is selected from one or combination of more than two of hemp flowers, hemp leaves, hemp roots, hemp stalk cores and hemp seed cakes.

15. The method according to claim 14, wherein the extraction part in step 1) is selected from hemp flowers and hemp leaves.

16. The method according to claim 1, wherein the hemp in step 1) is selected from one or combination of more than two of industrial hemp, intermediate hemp or medicinal hemp.

* * * * *